(12) United States Patent
Del Favero

(10) Patent No.: US 10,947,588 B2
(45) Date of Patent: Mar. 16, 2021

(54) RESTRICTION MEDIATED QUANTITATIVE POLYMERASE CHAIN REACTIONS

(71) Applicant: MULTIPLICOM N.V., Niel (BE)

(72) Inventor: Jurgen Del Favero, Niel (BE)

(73) Assignee: MULTIPLICOM N.V., Niel (BE)

( * ) Notice: Subject to any disclaimer, the term of this patent is extended or adjusted under 35 U.S.C. 154(b) by 548 days.

(21) Appl. No.: 15/319,279

(22) PCT Filed: Jun. 19, 2015

(86) PCT No.: PCT/EP2015/063832
§ 371 (c)(1),
(2) Date: Dec. 15, 2016

(87) PCT Pub. No.: WO2015/193483
PCT Pub. Date: Dec. 23, 2015

(65) Prior Publication Data
US 2017/0137865 A1 May 18, 2017

(30) Foreign Application Priority Data

Jun. 19, 2014 (WO) ............... PCT/EP2014/062971

(51) Int. Cl.
| | | |
|---|---|---|
| *C12Q 1/68* | (2018.01) | |
| *C12Q 1/686* | (2018.01) | |
| *C12Q 1/6853* | (2018.01) | |
| *C12Q 1/6851* | (2018.01) | |
| *C12Q 1/6818* | (2018.01) | |

(52) U.S. Cl.
CPC ........... *C12Q 1/686* (2013.01); *C12Q 1/6818* (2013.01); *C12Q 1/6851* (2013.01); *C12Q 1/6853* (2013.01); *C12Q 2525/131* (2013.01); *C12Q 2525/301* (2013.01); *C12Q 2537/143* (2013.01); *C12Q 2561/113* (2013.01); *C12Q 2565/101* (2013.01)

(58) Field of Classification Search
CPC ..... C12Q 1/686; C12Q 1/6818; C12Q 1/6853
See application file for complete search history.

(56) References Cited

U.S. PATENT DOCUMENTS

| | | | | |
|---|---|---|---|---|
| 2009/0068643 A1* | 3/2009 | Behlke | ................. | C12Q 1/6823 435/6.16 |
| 2009/0136956 A1* | 5/2009 | Merante | ............... | C12Q 1/6827 435/6.12 |
| 2010/0330574 A1* | 12/2010 | Whitman | ............. | C12Q 1/6853 435/6.1 |

FOREIGN PATENT DOCUMENTS

| | | |
|---|---|---|
| WO | WO 01/38570 A1 | 5/2001 |
| WO | WO 2010/139937 A1 | 12/2010 |
| WO | WO 2011/063388 A2 | 5/2011 |
| WO | WO 2011/141738 A1 | 11/2011 |
| WO | WO 2012/024639 A1 | 2/2012 |

OTHER PUBLICATIONS

International Search Report issued in International Patent Application No. PCT/EP2015/063832 dated Oct. 12, 2015.
Solinas et al., "Duplex Scorpion Primer in SNP analysis and FRET applications," Nucleic Acids Research, vol. 29, 2001, pp. 1-9.

* cited by examiner

Primary Examiner — David C Thomas
(74) Attorney, Agent, or Firm — Arent Fox LLP

(57) ABSTRACT

The present invention relates to the technical field of nucleic acid amplification using a Polymerase Chain Reaction (PCR). Specifically, the present invention relates to Polymerase Chain Reaction (PCR) primers and Polymerase Chain Reaction (PCR) nucleic acid amplification mixture and the use thereof in (quantitative) Polymerase Chain Reactions (PCR). Specifically, the present invention relates to Polymerase Chain Reaction (PCR) primers suitable for use in Restriction Mediated quantitative PCR (RM-qPCR) nucleic acid amplification reactions comprising a 5' Acceptor representing one member of a fluorescence resonance energy transfer (FRET) pair; A representing a nucleic acid sequence motif of 10 to 30 bp; 3-C representing a linker region comprised of at least three carbon atoms; B representing a double stranded restriction enzyme recognition site or a random nucleic acid sequence; A' representing a nucleic acid sequence motif of 10 to 30 bp being complementary to the nucleic acid sequence motif of A; and R-prim representing a nucleic acid sequence complementary to a target sequence in a nucleic acid sequence to be amplified.

12 Claims, 4 Drawing Sheets

RESTRICTION MEDIATED QUANTITATIVE POLYMERASE CHAIN REACTIONS

CROSS REFERENCE TO RELATED APPLICATION

Figure 1:

This application is a 35 U.S.C. 371 National Phase of PCT Application No. PCT/EP2015/063832 filed Jun. 19, 2015, which claims priority to PCT Application No. PCT/EP2014/062971 filed Jun. 19, 2014. The disclosure of these prior applications are hereby incorporated by reference in their entirety.

The present invention relates to the technical field of nucleic acid amplification using a Polymerase Chain Reaction (PCR). Specifically, the present invention relates to Polymerase Chain Reaction (PCR) primers, Polymerase Chain Reaction (PCR) nucleic acid amplification mixtures and the use thereof in, quantitative Polymerase Chain Reactions (PCR) and especially quantitative Polymerase Chain Reaction (qPCR) allowing amplification of multiple amplicons in a single Polymerase Chain Reaction (PCR).

A quantitative polymerase chain reaction (qPCR), also designated as a real-time polymerase chain reaction, is a laboratory technique generally used in Molecular Biology based on the polymerase chain reaction (PCR).

A polymerase chain reaction (PCR) generally consists of series of repeated, for example 15 to 60 times, cycles of temperature changes. These temperature cycles generally comprise at least three stages: the first stage, at around 95° C., allows for separation of the nucleic acid's double chain; the second stage, at a temperature of around 45 to 65° C., allows for binding of primers with a DNA template and the third stage, at between 68 to 75° C., facilitates polymerization carried out by a DNA polymerase thereby providing amplification of a target nucleic acid sequence. The specific temperatures and the time intervals used in each cycle depend on a number of parameters, such as enzymes used to duplicate the target DNA, concentration of divalent ions and deoxyribonucleotides (dNTPs) and annealing temperatures of the primers used.

A quantitative polymerase chain reaction (qPCR) is generally used to amplify, and quantify, a targeted DNA molecule. For one, or more, specific nucleic acid sequences in a DNA sample, quantitative PCR enables both detection and quantification. The quantity can be either an absolute number of copies or a relative amount when the amplification products are normalized to DNA input or reference genes. Quantitative PCR is generally carried out in a thermal cycler with the capacity to illuminate each sample with a beam of light of a specified wavelength and to detect the fluorescence emitted by the excited chromo- or fluorophore.

Multiplex polymerase chain reaction (Multiplex PCR) is a modification of polymerase chain reaction. A multiplex polymerase chain reaction uses two or more primer sets within a single PCR mixture to produce amplicons that are specific to different DNA sequences. By pursuing multiple targets at once, additional information may be gained from a single test run otherwise requiring several separate PCR reactions.

A combination of the above PCR assays, i.e. a quantitative polymerase chain reaction (qPCR) and multiplex polymerase chain reaction (multiplex PCR) would allow of real-time detection of multiple target sequences using a single amplification reaction thereby allowing, amongst others, efficient high through-put diagnosis on relatively small biological samples. However, using the presently known techniques, combining qPCR and multiplex PCR can only allow for the simultaneous amplification of a limited number of amplicons (up to 3 amplicons) in a single PCR reaction.

It is an object of the present invention, amongst other objects, to provide a combined use of a quantitative polymerase chain reaction (qPCR) and multiplex polymerase chain reaction (multiplex PCR) allowing for the simultaneous amplification of 4 or more amplicons such as more 10, more than 20, more than 40 or even more than 40 amplicons.

The above object of the present invention, amongst other objects, is met by the present invention by a novel PCR assay as outlined below and in the appended claims. The present novel PCR assay is designated herein as RM-QPCR or Restriction Mediated Quantitative PCR.

The above object of the present invention, amongst other objects, is, according to a first aspect, met by Polymerase Chain Reaction (PCR) primer suitable for use in Restriction Mediated quantitative PCR (RM-qPCR) nucleic acid amplification reactions, said primer has the following general structure:

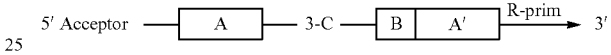

wherein:
5' Acceptor: represents one member of a fluorescence resonance energy transfer (FRET) pair
A: represents a nucleic acid sequence motif of 10 to 30 bp
3-C: represents a linker region comprised of at least three carbon atoms
B: represents a double stranded restriction enzyme recognition site or a random nucleic acid sequence;
A': represents a nucleic acid sequence motif of 10 to 30 bp being complementary to the nucleic acid sequence motif of A
R-prim: represents a nucleic acid sequence complementary to a target sequence in a nucleic acid sequence to be amplified.

The present inventors surprisingly discovered that the use of the above primer provides:
  by covalently attaching different members of a fluorescence resonance energy transfer (FRET) pair at the 5' part of the present primer and based on the availability of FRET combinations, the simultaneous detection of 4 to 6 amplicons per reaction
  by replacing the A and A' sequence motifs as well as corresponding donor oligonucleotide sequence with sequence motifs differing approximately 5° C. in melting temperature the simultaneous detection of 5 to 7 sets of sequences;
  by combining different R-prim labels and sequence motif melting temperatures the simultaneous amplification and detection of up to 40 amplicons per reaction.

The present invention uses Förster resonance energy transfer (FRET) pairs for detection. Förster resonance energy transfer (FRET), also designated as fluorescence resonance energy transfer (FRET), resonance energy transfer (RET) or electronic energy transfer (EET), is a mechanism based on energy transfer between two chromophores. A donor chromophore, initially in its electronic excited state, may transfer energy to an acceptor chromophore through non-radiative dipole-dipole coupling. The efficiency of this energy transfer is inversely proportional to the sixth power of the distance between donor and acceptor, making FRET extremely sensitive to small changes in distance. Measurements of FRET efficiency can be used to determine if two fluorophores are within a certain distance of each other. Below some fluorophores suitable to be used according to the present invention are provided:

| Fluorophore | Alternative Fluorophore | Excitation (nm) | Emission (nm) |
|---|---|---|---|
| FAM ™ (carboxyfluorescein) | | 495 | 515 |
| TET ™ (tetrachlorofluorescein) | CAL FLUOR ® Gold 540[A] | 525 | 540 |
| HEX ™ (hexachlorofluorescein) | JOE ™, VIC ™[B], CAL FLUOR ® Orange 560[A] | 535 | 555 |
| CY ®3[C] (Cyanine 3) | NED ®[B], QUASAR ® 570[A], OYSTER ® 556[D] | 550 | 570 |
| TMR (tetramethylrhodamine) | CAL FLUOR ® Red 590[A] | 555 | 575 |
| ROX ™ (rhoadamine X; carboxy-X-rhodamine) | LC ® red 610[E], (LightCycler ® Red 610) CAL FLUOR ® Red 610[A] | 575 | 605 |
| TEXAS RED ® (sulforhodamine 101 acid chloride) | LC ® red 610[E], (LightCycler ® Red 610), CAL FLUOR ® Red 610[A] | 585 | 605 |
| LC ® red 640[E] (LightCycler ® Red 640) | CAL FLUOR ® Red 635[A] | 625 | 640 |
| CY ®5[C] (Cyanine 5) | LC ® red 670[E], (LightCycler ® Red 670), QUASAR 670[A], OYSTER 645[D] | 650 | 670 |
| LC ® red 705[E] (LightCycler ® Red 705) | CY ®5.5[C] (Cyanine 5.5) | 680 | 710 |

| Quencher | Absorption Maximum (nm) |
|---|---|
| DDQ-1[A] | 430 |
| Dabcyl | 475 |
| ECLIPSE ®[B] | 530 |
| IOWA BLACK ® FQ[C] | 532 |
| BHQ ®-1[D] | 534 |
| QSY-7[E] | 571 |
| BHQ ®-2[D] | 580 |
| DDQ-11[A] | 630 |
| IOWA BLACK ® RQ[C] | 645 |
| QSY-21[E] | 660 |
| BHQ ®-3[D] | 670 |

According to a preferred embodiment of this first aspect of the present invention, the present double stranded restriction enzyme recognition site B is a 5 to 15 bp PspG1 restriction enzyme recognition sequence. PspG1 is a restriction enzyme recognizing and cleaving the dsDNA sequence: 'CCWGG/GGWCC'. The enzyme's optimal temperature is 75° C. and the enzyme is resistant to heat inactivation and, accordingly, is especially suitable to be used according to the present invention.

Another possibility is the use of other PspG1 like restriction enzymes or genome editing nuclease tools such as CRISPR, CAS9, Talen and ZFN or engineered hybrid meganucleases. Also RNase H based cleavage at the B-sequence can be envisaged by incorporating a RNA base at a specific B position of the R-prim based primer which can be cleaved, during the QPCR, by a thermostable RNase H based on the nature of RNaseH to cut at a RNA base in case of a perfect sequence similarity.

According to a second aspect, the present invention relates to Polymerase Chain Reaction (PCR) nucleic acid amplification mixtures comprising:

1) a template comprising a target sequence;
2) the present Polymerase Chain Reaction (PCR) primer;
3) a Polymerase Chain Reaction (PCR) primer S-prim allowing in combination with the present Polymerase Chain Reaction (PCR) primer amplification of at least one amplicon comprised in the target sequence;
4) a donor oligonucleotide having the following general structure

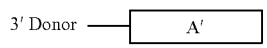

3' Donor —— A' wherein
5' Donor represents one member of a fluorescence resonance energy transfer (FRET) pair comprised of a light emitting molecule;
A' represents a nucleic acid sequence motif of 10 to 30 bp being complementary to the nucleic acid sequence motif of A;
5) restriction enzyme, preferably PspG1;
6) amplification enzyme and nucleotides.

Figure 3:
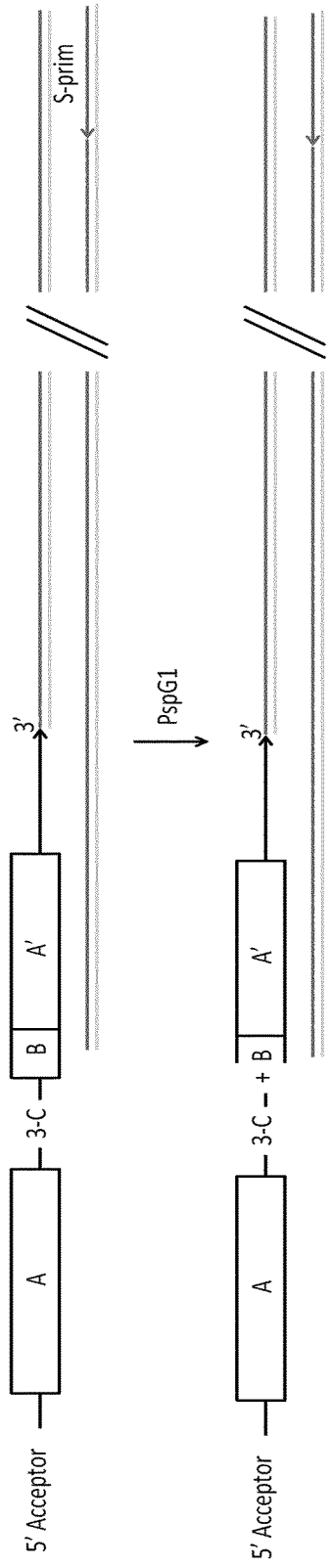

In the present amplification mixture, a detectable signal is obtained after cleavage of the restriction site B and a subsequent hybridization as is graphically depicted in FIG. 3.

In the present Polymerase Chain Reaction (PCR) nucleic acid amplification mixture, the present one member of a fluorescence resonance energy transfer (FRET) pair comprised of a quencher from the group consisting of Dabcyl, BHQ1, etc.

According to a third aspect, the present invention relates to the use of the present Polymerase Chain Reaction (PCR) primers or the present Polymerase Chain Reaction (PCR) nucleic acid amplification mixtures in a Polymerase Chain Reaction (PCR), preferably a quantitative Polymerase Chain Reaction (qPCR).

The present use according this aspect of the invention allows for the amplification of at least 4, preferably at least 6, more preferably at least 10 amplicons in a single nucleic acid amplification reaction such as 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39 amplicons.

Figure 2:
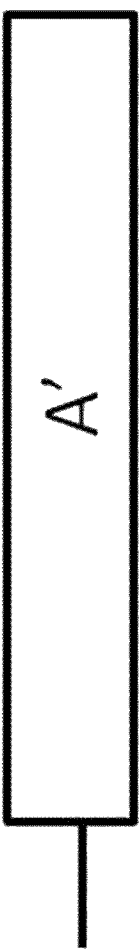
Figure 4:
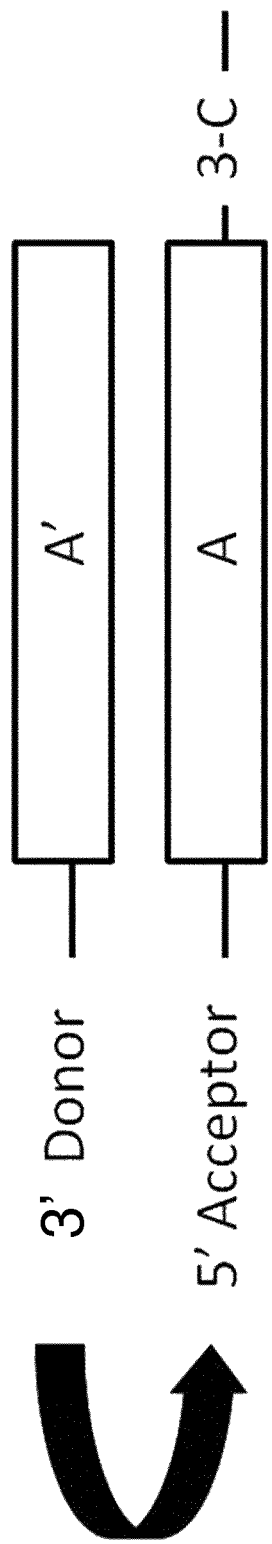

The present invention will be further illustrated in the example below of an especially preferred embodiment of the present invention. In the present description, reference is made to figures wherein:

FIG. 1: graphical representation of the general structure of an amplification primer according to the present invention;

FIG. 2: graphical representation of the general structure of a fluorophore donor probe according to the present invention;

FIG. 3: PCR and enzymatic digestion by PspG1, releasing the A sequencing motif;

FIG. 4: graphical representation of signal detection using the present amplification primer and donor probe;

EXAMPLE

The RM-QPCR is short for Restriction Mediated Quantitative PCR and is developed to realize the unmet need of highly multiplexed QPCR assays. Current QPCR methods (using standard equipment) only allow limited multiplexing of up to 2 or 3 amplicons per reaction. With RM-QPCR it is theoretically possible to derive multiplexes of up to 30-40 amplicons per reaction.

RM-QPCR:
1. Components:
   Each target amplicon is amplified by using a standard PCR primer (S-prim: 18-27 bp in length) and the present primer (R-prim: 70-80 bp in length: FIG. 1) composed of the following elements (from 3' to 5'):
   Amplicon specific sequence that in combination with the standard PCR primer will drive amplification if template DNA is present (R-prim).
   A' sequence motif (~20 bp) which is complementary to the A sequence motif.
   B sequence motif (~10 bp) containing the PspG1 restriction enzyme recognition sequence:
   PspG1 is a restriction enzyme recognising and cleaving the dsDNA sequence: 'CCWGG/GGWCC'. The enzymes optimal temperature is 75° C. and the enzyme is resistant to heat inactivation and hence can be used in a PCR reaction.
   Linker region containing at least 3 C-atoms
   A sequence motif (~20 bp) which is complementary to the A' sequence which contains a covalently attached fluorescent label (e.g. ROX)
2. Principle (Simplex PCR Reaction):
   A PCR reaction is set-up containing the following components:
   PCR buffer, dNTPs, Taq DNA polymerase
   S-prim and R-prim
   PspG1 enzyme
   Donor oligonucleotide
      The donor oligonucleotide has the sequence A' and hence is complementary to A.
      Contains a covalently attached fluorescent label (e.g. Fam or quencher)
   Upon successful amplification the single stranded B sequence motif will become double stranded leading to cleavage by PspG1 during the elongation step of the PCR (FIG. 2).
   Cleavage will result in the release of the single stranded A sequence motif containing a fluorescent label. This part of the R-prim remains single stranded during PCR since elongation cannot proceed over the linker sequence as depicted in FIG. 3.
   The PspG1 mediated release of the A sequence motif will result in hybridisation with the donor oligonucleotide allowing detection of amplification by FRET (Fluorescence Resonance Energy Transfer) by close proximity of the fluorescent label from the A sequence motif (acceptor) and the fluorescent label on the donor oligonucleotide (FIG. 4).
   Since intra-molecular hybridisation is favoured over inter-molecular hybridisation, FRET will only occur if the single stranded A sequence motif is physically removed from R-prim.
3. Principle (Multiplex PCR):
Multiplexing can be achieved by:
   Covalently attaching a different fluorescent label at the 5' of the R-prim
      Based on the availability of FRET combinations this can generate per R-prim and donor oligonucleotide 4 to 6 combinations enabling detection of 4 to 6 amplicons per reaction
   Replace A and A' sequence motif as well as corresponding donor oligonucleotide sequence with sequence motif differing ~5° C. in melting temperature
      Applying a ~5° C. melting temperature difference per set of sequence motives will result in 5 to 7 sets of sequences that can be used to detect amplicons based on melting temperature
   Combining different R-prim labels and sequence motif melting temperatures it is possible to multiplex up to ~40 amplicons per reaction.

The invention claimed is:
1. A Polymerase Chain Reaction (PCR) nucleic acid amplification mixture comprising:
   1) a template comprising a target sequence;
   2) a PCR primer comprising the following general structure:

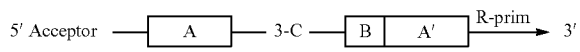

wherein:
   5' Acceptor: represents one member of a fluorescence resonance energy transfer (FRET) pair;
   A: represents a nucleic acid sequence motif of 10 to 30 bases;
   3-C: represents a linker region comprised of at least three carbon atoms;
   B: represents a double stranded restriction enzyme recognition site;
   A': represents a nucleic acid sequence motif of 10 to 30 bases being complementary to the nucleic acid sequence motif of A; and
   R-prim: represents a nucleic acid sequence complementary to a target sequence in a nucleic acid sequence to be amplified;
   3) a PCR primer S-prim providing, in combination with the PCR primer as defined in 2), amplification of at least one amplicon comprised in said target sequence;
   4) a donor oligonucleotide having the following general structure:

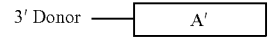

wherein
      A' represents a nucleic acid sequence motif of 10 to 30 bases being complementary to the nucleic acid sequence motif of A;
   5) a restriction enzyme; and
   6) amplification enzyme and nucleotides.
2. The PCR nucleic acid amplification mixture according to claim 1, wherein said one member of a fluorescence resonance energy transfer (FRET) pair is a fluorophore selected from the group consisting of FAM™ (carboxyfluorescein), TET™ (tetrachlorofluorescein), HEX™ (hexachlorofluorescein), CY®3 (Cyanine 3), TMR (tetramethylrhodamine), ROX™ (carboxy-X-rhodamine), TEXAS RED® (sulforhodamine 101 acid chloride), LC® red 640 (LightCycler® Red 640), CY®5 (Cyanine 5), a quencher, and LC® red 705 (LightCycler® Red 705).
3. The PCR nucleic acid amplification mixture according to claim 1, wherein the restriction enzyme is PspG1.
4. A method of performing Polymerase Chain Reaction (PCR) comprising amplifying a template comprising a target sequence with a PCR nucleic acid amplification mixture comprising:

1) a template comprising a target sequence;
2) a Polymerase Chain Reaction (PCR) primer comprising the following general structure:

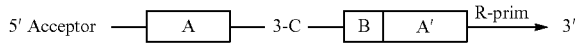

wherein:
  5' Acceptor: represents one member of a fluorescence resonance energy transfer (FRET) pair;
  A: represents a nucleic acid sequence motif of 10 to 30 bases;
  3-C: represents a linker region comprised of at least three carbon atoms;
  B: represents a double stranded restriction enzyme recognition site;
  A': represents a nucleic acid sequence motif of 10 to 30 bases being complementary to the nucleic acid sequence motif of A; and
  R-prim: represents a nucleic acid sequence complementary to a target sequence in a nucleic acid sequence to be amplified;
3) a PCR primer S-prim providing, in combination with the PCR primer as defined in 2), amplification of at least one amplicon comprised in said target sequence;
4) a donor oligonucleotide having the following general structure:

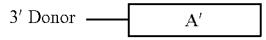

wherein
  A' represents a nucleic acid sequence motif of 10 to 30 bases being complementary to the nucleic acid sequence motif of A;

5) a restriction enzyme; and
6) amplification enzyme and nucleotides.

5. The method according to claim 4, wherein said PCR is a quantitative Polymerase Chain Reaction (qPCR).

6. The method according to claim 4, wherein said one member of a FRET pair is a fluorophore selected from the group consisting of FAM™ (carboxyfluorescein), TET™ (tetrachlorofluorescein), HEX™ (hexachlorofluorescein), CY®3 (Cyanine 3), TMR (tetramethylrhodamine), ROX™ (carboxy-X-rhodamine), TEXAS RED® (sulforhodamine 101 acid chloride), LC® red 640 (LightCycler® Red 640), CY®5 (Cyanine 5), a quencher, and LC® red 705 (LightCycler® Red 705).

7. The method according to claim 4, wherein the restriction enzyme is PspG1.

8. The method according to claim 4, wherein said PCR amplifies at least 4 amplicons in a single nucleic acid amplification reaction.

9. The method according to claim 4, wherein said PCR amplifies at least 6 amplicons in a single nucleic acid amplification reaction.

10. The method according to claim 4, wherein said PCR amplifies at least 10 amplicons in a single nucleic acid amplification reaction.

11. The PCR nucleic acid amplification mixture according to claim 1, wherein said double stranded restriction enzyme recognition site B on the PCR primer is a 5 to 15 bp PspG1 restriction enzyme recognition sequence.

12. The PCR nucleic acid amplification mixture according to claim 11, wherein said 5 to 15 bp PspG1 restriction enzyme recognition sequence on the PCR primer comprises the sequence motif "CCWGG" or "GGWCC" wherein W is A or T.

* * * * *